United States Patent [19]

Wheeler, Jr.

[11] 4,416,984
[45] Nov. 22, 1983

[54] STERILIZATION INDICATOR

[75] Inventor: Robert P. Wheeler, Jr., Keene, N.H.

[73] Assignee: Concord Laboratories, Inc., Keene, N.H.

[21] Appl. No.: 266,184

[22] Filed: May 22, 1981

[51] Int. Cl.$^3$ .......................... C12Q 1/22; C12M 1/00; C12M 1/24; C12M 1/18

[52] U.S. Cl. ...................................... 435/31; 435/287; 435/296; 435/300

[58] Field of Search .................. 435/31, 287, 290, 296, 435/299, 300, 301

[56] References Cited

U.S. PATENT DOCUMENTS

| | | | |
|---|---|---|---|
| 2,854,384 | 9/1958 | Beakley et al. | 435/31 X |
| 3,239,429 | 3/1966 | Menolasino et al. | 435/31 X |
| 3,440,144 | 4/1969 | Andersen | 435/31 |
| 3,585,112 | 6/1971 | Ernst | 435/31 |
| 3,616,263 | 10/1971 | Anandam | 435/296 X |
| 3,657,073 | 4/1972 | Burton et al. | 435/31 X |
| 3,661,717 | 5/1972 | Nelson | 435/31 |
| 3,752,743 | 8/1973 | Henshilwood | 435/31 X |
| 3,875,012 | 4/1975 | Dorn et al. | 435/296 X |
| 4,291,122 | 9/1981 | Orelski | 435/31 |

Primary Examiner—Robert J. Warden
Attorney, Agent, or Firm—Sewall P. Bronstein; George W. Neuner

[57] ABSTRACT

A sterilization indicator for testing the effectiveness of a sterilization process and a sterilization process using such an indicator are described. The indicator comprises a first compartment having at least one open end; a gas-permeable, bacteria-impermeable closure covering said open end; said first compartment containing a number of viable microorganisms that are resistant to a related sterilization process; a second compartment moveable with respect to said first compartment; said second compartment having a predetermined quantity of nutrient medium for promoting the growth of said microorganisms; separation means for sealing the nutrient medium in said second compartment; communications means for providing communication between said first compartment and said second compartment when it is desired to contact said microorganisms with said nutrient medium; and a detector composition contained in one of said compartments that is capable of undergoing a detectable change in response to the growth of said microorganisms.

13 Claims, 10 Drawing Figures

U.S. Patent  Nov. 22, 1983  4,416,984
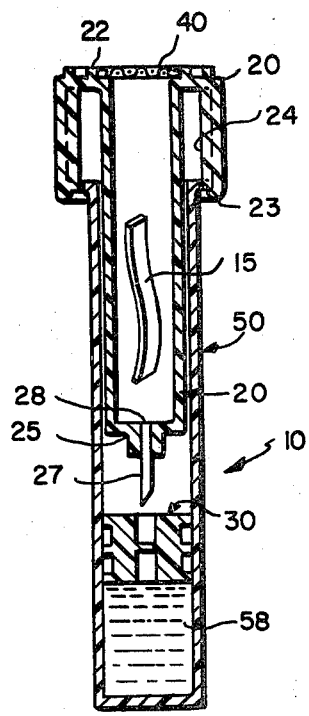
FIG.1
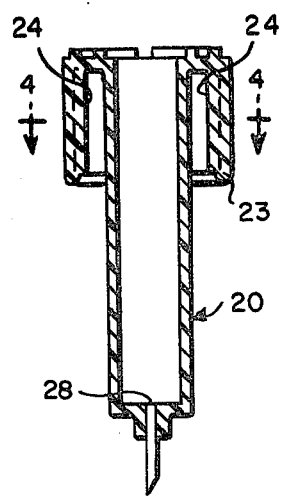
FIG.2
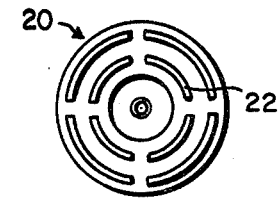
FIG.3
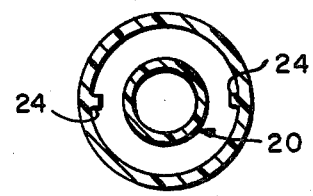
FIG.4
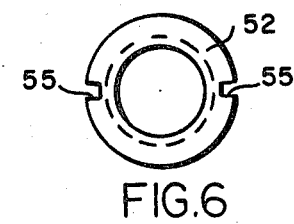
FIG.6
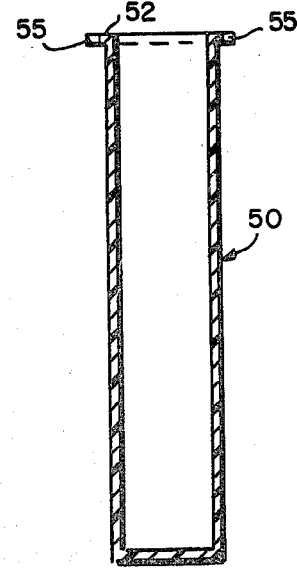
FIG.5
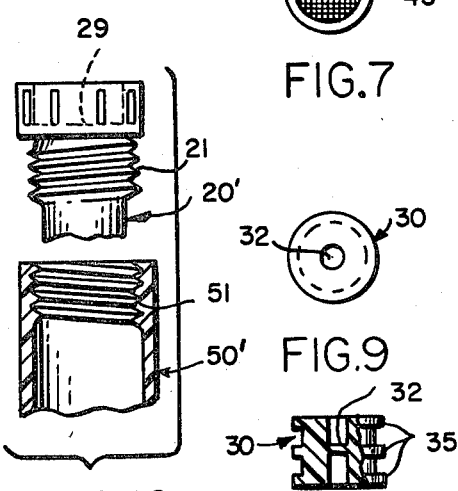
FIG.10
FIG.7
FIG.9
FIG.8

STERILIZATION INDICATOR

FIELD OF THE INVENTION

This invention relates to an apparatus and method for checking and testing the effectiveness of sterilization, and particularly to an apparatus containing a sterlization indicator comprising bacterial spores or the like.

BACKGROUND OF THE INVENTION

In hospitals, clinics and the like, it has been standard practice to sterilize various products such as gowns, drapes, sheets, dressings, and other articles, prior to use by placing them in an autoclave where they are subject to steam sterilization. This practice is necessary to avoid infection and prevent contamination from the use of such articles where the same are not in a sterile condition and is particularly important where the articles have previously been used in the care of other patients.

Ethylene oxide sterilization is typically utilized in hospitals or laboratories for treating articles, for example of plastic, paper, rubber or the like which cannot withstand heat sterilization. Sterilization is effected when ethylene oxide reacts with contaminating microorganisms to kill or inactivate them.

Medical materials such as gauzes, bandages, or absorbent cotton, or surgical instruments such as injectors, scalpels, or scissors have hitherto been used after they have been sterilized with dry heat, pressure steam, or by boiling, using a sterilizer in the hospital. However, they have recently been supplied to users (such as hospitals and medical practioners) in a hermetically sealed sterilized style after they have been completely sterilized in the factory of the manufacturer for medical and surgical materials, instead of sterilizing them immediately prior to their use in hospitals or the like.

As there is no visual way of determining whether a particular article is sterile or not, it has been the practice to use a color change indicator with the article when placed in the steam sterilization chamber. The color change indicator changes under the sterilizing conditions of the autoclave, thus indicated that the particular article or package has been passed through the sterilizing cycle. The indicator may be in the form of a ribbon or card to which a color change ink has been applied.

However, even though such indicators show whether the materials have been exposed to the sterilization process, there is no indication of whether the process was effective. One way of determining whether or not sterilizing has been effective is to include in the sterilizer a biological test strip. Such a strip consists of a selected level of organisms having a resistance greater than is likely to be encountered on the articles being sterilized. Organisms that are particularly difficult to destroy are selected as the control standard, e.g., *Bacillus subtilis* var. *Niger* and *Bacillus stearothermophilus.* After the sterilization cycle is completed, the strip is sent to the laboratory to determine if the organisms on the strip are dead thereby indicating sterilization effectiveness. While this method is reliable, it has the disadvantage of requiring several days or longer before the results are determined.

In addition to the time delay, the use of a biological test strip as an indicator has required a trained technician and clean room facilities for conducting the tests. In spite of all the precautions, using trained technicians and clean rooms, on occasion the tests are contaminated and false positives are obtained because of human error. The test must be considered positive and the product resterilized and retested causing delayed deliveries, increased costs, and the like.

However, the only way to be sure that the sterilization was effective is to run a biological test. Thus, improved tests are desired that would reduce or eliminate false positives and that would reduce or eliminate the requirement for trained technicians and or clean room environments for conducting the tests. Several attempts to provide a self-contained sterilization test have been described, for example, in U.S. Pat. Nos. 2,854,384; 3,068,154; 3,239,429; 3,346,464; 3,440,144 and 3,667,717. However, to date none of the solutions described previously has provided an entirely satisfactory self-contained sterilization effectiveness test indicator.

SUMMARY OF THE INVENTION

The present invention provides a unitary sterilization indicator for determining the effectiveness of a sterilization process and a method for checking the effectiveness of a sterilization process using the indicator. The sterilization indicator of this invention comprises:

a first compartment having at least one open end;

a gas-permeable, microorganism-impermeable closure covering said open end;

said first compartment containing a number of viable microorganisms:

a second compartment, said first compartment and said second compartment being moveable with respect to each other;

said second compartment containing a predetermined quantity of nutrient medium for promoting the growth of said microorganisms;

separation means for sealing the nutrient medium in said second compartment;

communication means for providing communication between said first compartment and said second compartment when it is desired to contact said microorganisms with said nutrient medium;

a detector composition contained on one of said compartments that is capable of undergoing a detectable change in response to the growth of said microorganisms.

BRIEF DESCRIPTION OF THE DRAWINGS

The invention may be more easily understood by reference to the accompanying drawings in which:

FIG. 1 is a partial cross-sectional view of one embodiment of an apparatus of the present invention including a culture strip;

FIG. 2 is a cross-sectional view of the inner compartment of FIG. 1 without culture strip;

FIG. 3 is a plan view of the compartment illustrated in FIG. 2;

FIG. 4 is a cross-sectional view of the compartment of FIG. 2 taken along lines 4—4 of FIG. 2;

FIG. 5 is a cross-sectional view of the outer compartment of FIG. 1;

FIG. 6 is a plan view of the compartment illustrated in FIG. 5;

FIG. 7 is a plan view of the closure disc of FIG. 1;

FIG. 8 is a partial cross-sectional view of the sealing member of FIG. 1.;

FIG. 9 is a plan view of the sealing member of FIG. 8.

FIG. 10 is an expanded partial cross-sectional view illustrating a preferred embodiment of the invention.

DESCRIPTION OF THE INVENTION

The sterility indicator of this invention may employ various microorganisms such as, for example, bacteria, fungi protozoa, and the like. Examples of specific bacteria that can be employed include *Bacillus subtilis, Bacillus stearothermophilus, Clostridium sporogenes*, etc. and the like. Examples of specific fungi that can be employed include Neurospora, Pithomyces, Daldinia, etc. and the like. Preferably, bacteria and fungi that exist in both "spore" and "vegetative" states are employed. Bacteria and fungi are commonly more resistant to sterilization in the spore state than in the vegetative state. Thus, to provide a margin of safety, bacteria and fungi in the spore state are preferably used in this invention. In selecting the particular microorganism to be used, a further margin of safety is provided by preferably employing microorganisms that are more highly resistant to the sterilization conditions than are the microorganisms intended to be killed during the sterilization cycle.

The particular microorganism is selected, as aforesaid, in accord with the method of sterilization used such as heat, gas, radiation, etc. It should be appreciated that a single sterility indicator may contain more than one species of microorganism, each species being resistant to a different method of sterilization.

With reference to the figures, one embodiment of a sterility indicator in accord with the present invention is illustrated in FIG. 1. The sterility indicator 10 comprises a first compartment 20 partially surrounded by a second compartment 50 that is closed by engagement with the first compartment 20. The first compartment 20 is covered by a closure member 40 that is gas-permeable but impermeable to microorganisms.

Inside the first compartment 20 is located a strip 15 containing microorganisms of a species resistant to sterilization. Opposite the covered end is a partially open end that communicates with the second compartment 50 through opening 28. The partially open end of the first compartment 20 has a reduced diameter portion 25 adapted to engage a cannula 27. Alternately, the cannula 27 can be press-fit into opening 28 as illustrated in FIG. 2, or may be integrally molded with the first compartment 20.

One end of the first compartment 20 is adapted for receiving the open end of the second compartment 50 so that flange 52 of the second compartment engages the inward projecting flange 23 of the first compartment to join the compartments together.

The indicator components can be made from any suitable material. Plastics are preferred for ease of handling. It is desirable that clear materials be used so that the culture media can be readily seen to read the test results.

A sealing member 30 is inserted into the second compartment 50 providing a sealed chamber 58 for nutrient medium to promote the growth of the microorganism carried on the strip 15 contained in the first compartment 20. The sealing member 30 thus prevents the nutrient medium from premature contact with the microorganisms. The sealing member 30 has three circular ribs 35 that form the seal and stabilize it inside the second compartment. The sealing member 30 is also designed with a thin portion 32 that is easily engaged and punctured by the cannula 27 to provide access to the spore strip 15 for the nutrient medium contained in chamber 58. The sealing member can be made from any suitable elastomeric material that is not detrimentally affected by the sterilization process. The number of ribs 35 may be varied, for instance two or four ribs, or more, to provide adequate sealing.

Preferably, the sterility indicator is adapted with means for preventing activation so that the sealing member is not prematurely punctured. In the sterility indicator illustrated in FIG. 1, this is accomplished by providing one or more ribs 24, in this case two ribs, located on the first compartment 20 to prevent activating movement between the compartments and, thus, avoid premature puncturing of sealing member 30. When it is desired to activate the indicator by puncturing the sealing member, the ribs 24 are aligned with corresponding openings 55 in the flange 52 of the second compartment 50 and the seal can be readily punctured to allow communication between chamber and the first compartment 20 containing spore strip 15.

The sterility indicator 10 is assembled by filling a predetermined quantity of nutrient medium for the microorganism into the second compartment 50. Any suitable nutrient medium for the microorganism can be used. An example of a suitable nutrient medium is Tryptic Soy Broth. Other suitable media are well known to those skilled in the art.

After the nutrient medium is placed in the second compartment 50, the sealing member 30 is inserted a sufficient distance so that the first compartment 20 can be inserted and engaged with the second compartment through the coupling of flanges 23 and 52 without puncturing the thin portion 32 of the sealing member.

After sterilization of the partially assembled indicator, a spore strip 15 carrying a resistant microorganism is inserted in the first compartment 20 and closure 40 is snapped into ring 22. The closure 40 comprises an annular ring 45 holding a material 42 that is gas-permeable and/or steam-permeable (for steam sterilization) but impermeable to microorganisms. The material preferably is selected from filter media capable of filtering out microorganisms while allowing the transmission of gases. Filter materials having ratings less than 0.5 μm are preferred, and membrane materials are particularly preferred. Alternatively, a filter comprised of a suitable depth of cotton or synthetic fiber can be used. One-eighth inch thickness of material having a 10 micron rating has been found satisfactory.

In the practice of this invention the microorganisms are preferably carried on an absorbant material. Filter paper is particularly useful as the carrier. However, pieces of material simulating particular products to be sterilized may be preferred as the carrier in some circumstances.

A detector composition is contained in one of the compartments of the sterility indicator. The detector composition is a composition that undergoes a detectable change in response to the growth of the microorganisms. Preferably the detectable change is a visible change such as a change in color so that the change is readily apparent to an unskilled observer. However, other detectable changes requiring instrumentation are useful, particularly in automated operations.

If the detector composition is to be placed in the second compartment, it is added to the nutrient medium and sterilized with the partially assembled indicator as described above. If the detector composition is to be placed in the first compartment it can be added separately or carried on the spore strip.

Suitable detector compositions are well known in the art and are selected depending on the biological process expected from the particular microorganism and nutrient medium used in the test. Typically, as microorganisms such as bacteria metabolize, the pH drops due to acidic metabolic products and the production of $CO_2$. Thus suitable pH indicators such as Brom Thymol Blue, Methylene Blue, Bromocresol Purple, Phenol Red, and the like, etc. can be used depending on specific conditions.

Because bacteria reach a stationary phase in which growth is regulated by limiting factors such as growth nutrients, dissolved oxygen, etc., the bacteria die and lyse releasing alkaline endotoxins and cell constituents. This shifts the pH alkaline resulting in false negatives. Combinations of indicators such as Brom Thymol Blue and Phenol Red have been found to overcome this problem.

It has also been found that adding glucose to the Tryptic Soy Broth medium tends to increase acid production and enhance the color transition.

In use the sterilization indicator in accord with the present invention is placed in the sterilization chamber along with the materials and/or objects being sterilized and the sterilization cycle is completed. The sterilization chamber is then unloaded and the sterilization indicator is activated by aligning ribs 24 with openings 55 in flange 52 and the two compartments are moved axially with respect to each other so that the thin portion 32 of sealing member 30 is pierced by cannula 27 and chamber 58 is open to the first compartment 20. Instead of providing a thin portion 32 in the sealing member, a ball bearing or other plug may be used to seal the passageway. This plug is pushed out by engagement of the cannula with the sealing member to open communication between compartments. Nutrient medium can then flow from chamber 58 into compartment 20 to contact the spore strip 15 and promote the growth of any viable microorganisms.

In a preferred embodiment as illustrated in FIG. 10, the first compartment 20' and second compartment 50' are each provided with threaded portions 21 and 51, respectively. After the sterilization cycle this preferred indicator is activated by turning the first compartment 20' into the second compartment 50' by means of threaded portions 21 and 51, thus causing the thin portion 32 of sealing member 30 to be punctured. The top portion of compartment 20' is formed with a chamber 29 which will hold a depth filter.

A cap maybe provided with the sterilization indicator 10 so that the end of the first compartment 20 can be closed in order to prevent the medium from evaporating during incubation. Prefereably the cap is attached to the second compartment 50 by means of a tether or the like so that the cap cannot be separated from the indicator unit or lost. In addition, attaching the cap to the second compartment provides a means to prevent closure of the first compartment until after activation of the indicator unit by selecting the appropriate length for the tether.

The activated sterility indicator is then incubated for a predetermined length of time depending on the particular sterility specifications being met. After incubation the sterility indicator is examined for any detectable change indicated by the detector composition as a result of the growth of microorganisms that survived the sterilization cycle. If any detectable change is found the sterilization cycle must be repeated.

Although the invention has been described in detail with reference to the preferred embodiments thereof, it will be appreciated that those skilled in the art, upon reading this disclosure, will be enabled to make modifications and improvements within the spirit and scope of this invention.

For instance, the compartment containing the microorganisms may be closed with a seal and a cannula located in the other compartment for piercing the seal to allow contact of the nutrient medium with the microorganisms. Further, other geometric and structural configurations for the compartments can be readily adapted to practice the invention by those skilled in the art. Also, for instance, the sealing member may have a bore and a plug such as a small ball bearing that is pushed out to open the passageway.

What is claimed is:

1. A sterilization indicator comprising:
    a first compartment having at least one open end;
    a gas-permeable, bacteria-impermeable closure covering said open end;
    said first compartment containing a number of viable microorganisms;
    a second compartment, said first and second compartments being moveable with respect to each other;
    said second compartment having a predetermined quantity of nutrient medium for promoting the growth of said microorganisms;
    separation means separating the nutrient medium in said second compartment from said microorganisms in said first compartment until it is desired to contact said microorganisms with said nutrient medium;
    communication means for providing communication between said first compartment and said second compartment by penetrating said separating means when it is desired to contact said microorganisms with said nutrient medium;
    activation means for activating said communication means by relative movement between said first and second compartments to provide communication between said first compartment and said second compartment without breaking said second compartment by engaging and penetrating said separation means; and
    a detector composition contained in one of said compartments that is capable of undergoing a detectable change in response to the growth of said microorganisms.

2. The sterilization indicator of claim 1, said sterilization indicator further comprising means for preventing communication between said first compartment and said second compartment until it is desired to contact said microorganisms with said nutrient medium.

3. The sterilization indicator of claim 1 wherein said microorganisms are carried on a substrate.

4. The sterilization indicator of claim 3 wherein said substrate is an absorbent material.

5. The sterilization indicator of claim 1 wherein said separation means is an elastomeric stopper.

6. The sterilization indicator of claim 1 wherein said closure comprises a membrane.

7. The sterilization indicator of claim 1 wherein said closure contains openings the average size of which are 0.5 $\mu$m or less.

8. The sterilization indicator of claim 1 wherein said detector composition undergoes a visible change in response to the growth of said microorganisms.

9. The sterilization indicator of claim 8 wherein said visible change is a change of color.

10. The sterilization indicator of claim 1 wherein said first compartment is moveable axially in said second compartment, said separation means is an elastomeric plug, said communication means is a cannula, and said actuating means comprises means for moving said first compartment axially with respect to said second compartment so that said cannula engages said elastomeric plug to open a passageway between said first and second compartments.

11. The sterilization indicator of claim 1 wherein said activation means comprises a first threaded portion on said first compartment and a second threaded portion on said second compartment that is compatible with the first threaded portion.

12. A method for checking the effectiveness of a sterilization process, said method comprising:

placing a sterilization indicator into a sterilization chamber along with objects to be sterilized, said sterilization indicator comprising a first compartment having at least one open end; a gas-permeable, bacteria-impermeable closure covering said open end; said first compartment containing a number of viable microorganisms; a second compartment moveably engaged with said first compartment; said second compartment having a predetermined quantity of nutrient medium for promotion of growth of said microorganisms; separation means separating the nutrient medium in said medium in said second compartment from said microorganisms in said first compartment until it is desired to contact said microorganisms with said nutrient medium; communication means for providing communication between said first compartment and said second compartment by penetrating said separating means when it is desired to contact said microorganisms with said nutrient medium; activation means for activating said communication means to provide communication between said first compartment and said second compartment without breaking said second compartment by engaging and penetrating said separation means; and a detector composition contained in one of said compartments that is capable of undergoing a detectable change in response to the growth of said microorganisms;

removing the sterilization indicator from the sterilization chamber along with the objects being sterilized after completion of the sterilization cycle;

activating the sterilization indicator to contact the microorganisms with the nutrient medium;

incubating the sterilization indicator for a predetermined period of time to promote the growth of the microorganisms; and examining the sterilization indicator for said detectable change in response to the growth of the microorganisms.

13. The method for checking the effectiveness of a sterilization process according to claim 12 wherein said detector composition undergoes a visible change and the examining step comprises visual examination of the indicator to determine whether any change has occurred.

* * * * *